United States Patent [19]

Carroll et al.

[11] Patent Number: 5,264,574
[45] Date of Patent: Nov. 23, 1993

[54] PREPARATION OF OXAZABOROLIDINE BORANE COMPLEX

[75] Inventors: James D. Carroll, Carteret; David J. Mathre, Skillman; Edward G. Corley, Old Bridge; Andrew S. Thompson, Mountainside, all of N.J.

[73] Assignee: Merck & Co., Inc., Rahway, N.J.

[21] Appl. No.: 862,647

[22] Filed: Apr. 3, 1992

[51] Int. Cl.$^5$ .................... C07F 5/02; C07D 235/02
[52] U.S. Cl. .............................. 546/13; 548/110
[58] Field of Search ......................... 548/110; 546/13

[56] References Cited

U.S. PATENT DOCUMENTS 5,039,802 8/1991 Blacklock et al. ................. 546/165

OTHER PUBLICATIONS

CA 108:75026v A stable . . . of Ketones, Applications to multistep synthesis. Corey et al., p. 644, 1988.
CA 111:115277y Boron-11 nuclear . . . borates, Contreras, p. 672, 1989.
CA 114:62157n A practical . . . oxazaborolidines. Mathre et al., p. 697, 1991.
CA 115:232503n Arylation . . . reduction. Blacklock et al., p. 977, 1991.
Mathre et al., J. Org. Chem. 56, 751-762 (1991) A practical entioselective . . . oxazaborolidines.

*Primary Examiner*—Mary C. Lee
*Assistant Examiner*—Joseph K. McKane
*Attorney, Agent, or Firm*—Sylvia A. Ayler; Joseph F. DiPrima; Mark R. Daniel

[57] ABSTRACT

Oxazaborolidine-borane complexes are prepared by adding a $C_{5-8}$alkane, typically hexane, to an aged solution of oxazaborolidine and a source of borane such as borane-dimethyl sulfide or gaseous diborane to crystallize the oxazaborolidine complex.

14 Claims, No Drawings

PREPARATION OF OXAZABOROLIDINE BORANE COMPLEX

BACKGROUND OF THE INVENTION

U.S. Pat. No. 5,039,802, awarded to T. J. Blacklock, T. K. Jones, D. J. Mathre and L. C. Xavier, discloses that tetrahydro-1-methyl-3,3-diphenyl-1H,3H-pyrrolo[1,2--c][1,3,2]oxazaborole--borane (1) is a stable, free flowing, crystalline solid. In contrast, β-methyl oxazaborolidine (2) is extremely sensitive to the presence of moisture. Both the (R) and (S) enantiomers of 1 have been utilized as enantioselective catalysts for the reduction of prochiral ketones. The yield and enantioselectivity of reductions using catalytic amounts 1 are identical to those using freshly prepared toluene solutions of 2. When used stoichiometrically (0.5 mol 1 per mol of ketone) the enantioselectivity is superior to the catalytic procedure. In this patent application we identify the parameters necessary to maximize the isolated yield of 1.

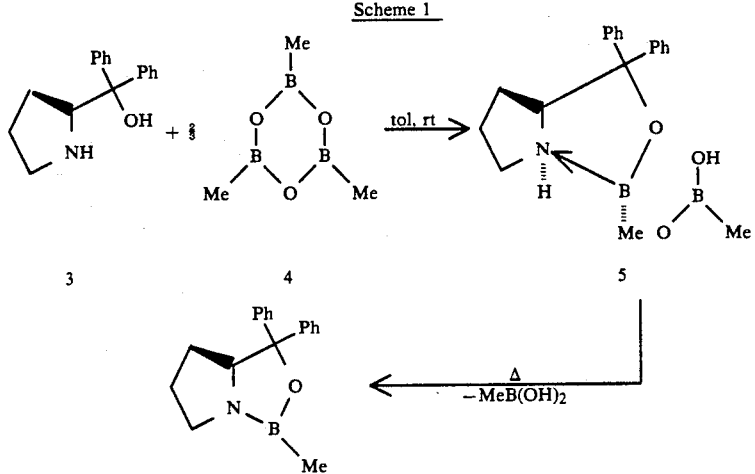

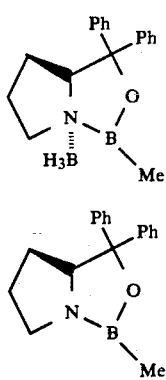

A detailed synthesis of β-methyl oxazaborolidine 2 has been described in above-mentioned U.S. Pat. No. 5,039,802. The protocol described in this patent involved addition of 0.667 mol of trimethylboroxine (4) to diphenylprolinol (3) in dry toluene, aging for 0.5 hour at 20°-25° C., and then heating to reflux for 1-2 hours. This was followed by subsequent additions of toluene and concentrations (Scheme 1). Although this procedure works well on a small scale (especially when using a Dean-Stark trap for removal of water) we began to encounter problems driving the reaction to completion on a larger scale. Indeed, we found the 1-2 hour age at reflux to be unnecessary, and may in fact be deleterious for the clean production of oxazaborolidine 2.

Heating intermediate 5 produces oxazaborolidine 2 and methylboronic acid. Under these same conditions methylboronic acid is converted to trimethylboroxine and water, which co-distill with the toluene. Removal of trimethylboroxine and water drives the reaction to completion. Water can also react with oxazaborolidine 2 to afford the unstable water adduct 6 which quickly disproportionates to intermediate 5 and diphenylprolinol 3 (Scheme 2). The 1-2 hour at reflux (without efficient removal of water) provides an opportunity for water to react with the oxazaborolidine. This becomes a more significant problem at larger scales when the time required to heat the mixture to reflux increases. Simply removing the 1-2 hour age at reflux from the process minimizes this problem. We disclosed this modification in our copending U.S. patent application Ser. No. 730,316 filed Jul. 15, 1991.

In addition, one can easily recover a batch containing residual diphenylprolinol, intermediate 5, or water adduct 6. This is achieved by addition of a second charge of trimethylboroxine (5-10 mol %) followed by a toluene flush. The ability to recover (or regenerate) a batch in this manner provides an important safety net, especially when large quantities of the oxazaborolidine are involved.

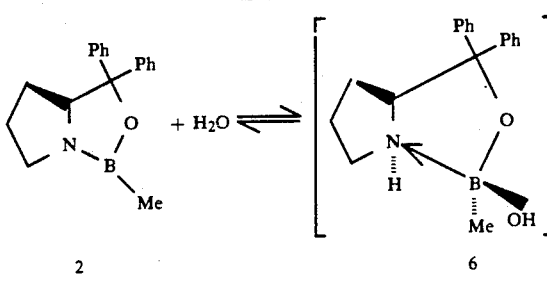

-continued
Scheme 2

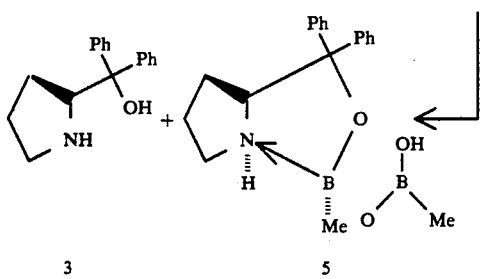

The original procedure to prepare oxazoborolidine—borane complex 1 disclosed in U.S. Pat. No. 5,039,802 involved addition of 2 mol of borane-dimethyl sulfide (BMS) to a toluene solution of oxazoborolidine 2. Removal of dimethyl sulfide using a nitrogen sweep drives the equilibrium, and at an undefined point the product would crystallize (Scheme 3). Larger batches required longer times to remove the foul smelling dimethyl sulfide. An additional concern when using a nitrogen sweep is the loss of free borane. This makes accurate charging of the BMS difficult.

Scheme 3

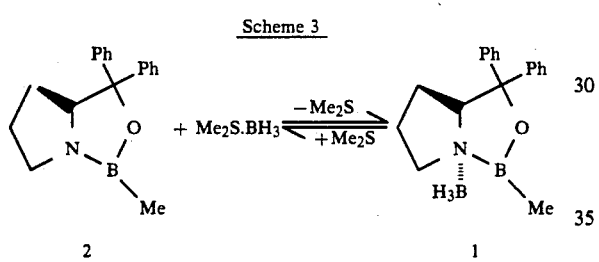

OBJECTS OF THE INVENTION

It is, accordingly, an object of the present invention to provide an improved process for the preparation of oxazoborolidine-borane complexes. Another object is to provide a process that allows recovery of a greater yield of the desired oxazoborolidine-borane complex. A further object is to provide a process that requires a lesser amount of BMS relative to the amount of oxazoborolidine. Yet another object is a method that minimizes loss of free borane. These and other objects of the present invention will be apparent from the following description.

SUMMARY OF THE INVENTION

It has now been found that oxazoborolidine-borane complexes can be formed in improved fashion by adding a $C_{5-8}$alkane to an aged solution of oxazoborolidine and a source of borane such as BMS or gaseous diborane to crystallize the oxazoborolidine-borane complex.

DETAILED DESCRIPTION

The present invention relates to the preparation of oxazoborolidine-borane complexes of formula V according to the reaction scheme shown on the following page. The starting material is a diarylprolinol sulfate of formula I, wherein Ar is phenyl, phenyl substituted in the meta- and/or para-positions with from 1 to 3 of (i) halogen, e.g., F, Cl or Br, (ii) $CF_3$, (iii) $C_{1-4}$alkyl or (iv) $C_{1-4}$alkoxy;

$R^1$ and $R^2$ are independently H, $C_{1-3}$alkyl, or $R^1$ and $R^2$ together with the carbon atoms to which they are bonded form a benzo group or a double bond;

R is $C_{1-4}$alkyl or Ar; and n is 1 or 2.

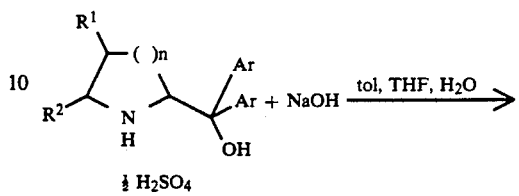

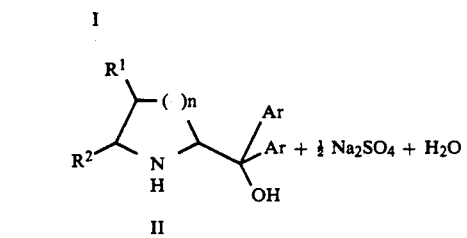

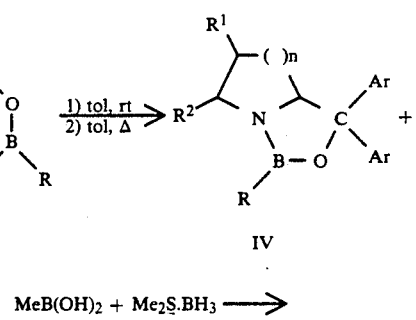

The compounds of formula V are prepared by the following reaction scheme. An (R)- or (S)-diarylprolinol sulfate of formula I in a mixture of water and an organic solvent such as, for example, THF, dimethoxyethane or a water-miscible alcohol is reacted with an alkali, e.g., NaOH, KOH, $Mg(OH)_2$ or $Ca(OH)_2$, at temperatures of from about 5° C. to about 40° C., preferably at from about 15° C. to about 30° C., and most preferably at from about 20° C. to about 25° C. until all of the solid dissolves, typically in from about 10 minutes to about 1 hour. At least equimolar amounts of alkali are used, and preferably a molar excess of alkali is used. After the solid dissolves, an aromatic organic solvent, e.g., benzene, toluene, xylene or chlorobenzene, is added. The volume of aromatic organic solvent is preferably at least about equal to the volume of the reaction mixture and preferably is about twice that of the reaction mixture. The resulting mixture is stirred for an additional period of time that is approximately equal to the time it took for all of the solid to dissolve. The entire mixture is then filtered.

The lower (aqueous) layer of the filtrate is removed and the organic layer is washed with water and then removed, preferably at elevated temperatures of from about 25°–50° C., preferably from about 35°–40° C. The organic layer is concentrated, e.g., by distillation, to about ⅓ its volume both to remove the solvent (THF, dimethoxyethane or water-miscible alcohol) and to azeotropically dry the solution. The concentration begins with a pot temperature of about 85° C. which is slowly increased to about 110° C. The solution of the (R)- or (S)-diaryl-prolinol II (free base) is cooled and stored under an inert atmosphere, with vigorous exclusion of moisture. The free base is diluted with a dry aromatic organic solvent such as, for example, benzene, toluene or xylene in an amount that is approximately equal to the post concentration volume of the organic layer, followed by controlled addition of the boroxine III over a period of from about 15 minutes to about 2 hours to produce the oxazaborole IV. The boroxine III can be added neat or as a solution in THF or an aromatic organic solvent such as, for example, benzene, toluene or xylene. The solution is then diluted with additional aromatic organic solvent as above and concentrated to about ⅓ the starting volume.

To a stirred solution of the concentrated oxazaborole solution is added an equimolar or slight molar excess, typically from about 1.1 to about 1.3 mol, of BMS or gaseous diborane over a short period of time, usually from 5 minutes to about 30 minutes. The mixture is then aged for from about 10 minutes to about 2 hours, typically about 0.5 hour, at from about 10° C. to about 35° C., preferably at from about 20° C. to about 25° C. Then a C$_{5-8}$ straight or branched chain alkane, e.g., pentane, 2-methylbutane, hexane, 2-methylpentane, 3-methylpentane, heptane, 2,3-dimethylpentane, 2,4-dimethylpentane, 2-methylhexane, 3-methylhexane, 4-methylhexane, octane, 2,3-dimethylhexane, 2,4-dimethylhexane, 2,5-dimethylhexane, 2-methylheptane, 3-methylheptane, 3-methylheptane or 4-methylheptane, is added slowly over a period of from about 30 minutes to about 2 hours, typically about 1 hour. The mixture is aged for a similar period of from about 30 minutes to about 2 hours, typically about 1 hour at a temperature of from about 10° C. to about 35° C., preferably at from about 20° C. to about 25° C. The mixture is cooled and aged at from about 0° C. to about −20° C. for from about 1 hour to about 10 hours, preferably at about −10° C. for about 3.5 hours. The mixture is filtered cold, washed with dry C$_{5-8}$ alkane and dried to yield the end product of formula V.

The foregoing process has several important advantages over the prior art processes:

1) Lesser amount of the costly and odorous BMS reagent are used;

2) The necessity of using a nitrogen sweep to remove excess BMS is eliminated;

3) Crystallization of the product is used to drive the equilibrium.

The following examples illustrate the present invention without, however, limiting the same thereto.

EXAMPLE 1

Preparation of (S)-Tetrahydro-1-methyl-3,3-diphenyl-1H,3H-pyrrolo[1,2-c][1,3,2]oxazaborole Reaction Scheme:

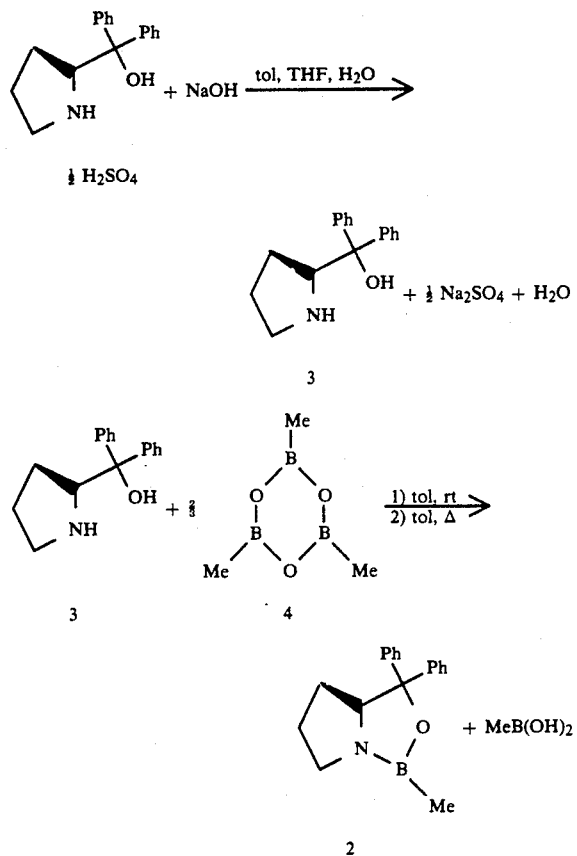

Materials:

| | | | | |
|---|---|---|---|---|
| (S)-Diphenylprolinol sulfate (Pilot Plant Batch #1–9) | 302.4 g/mol | 303 g | 1.00 mol | 1.00 equiv |
| Tetrahydrofuran (THF) | | 1.0 L | | |
| Toluene | | 7.0 L | | |
| Aqueous Sodium Hydroxide | 5.0 M | 400 mL | 2.00 mol | 2.00 equiv |
| Water (Merck, deionized) | | 1.1 L | | |
| Trimethylboroxine (Aldrich; d = 0.898 g/mL) | 125.54 g/mol | 96 g | 0.765 mol | 1.15 equiv |
| Celite | | 20 g | | |
| (S)-Tetrahydro-1-methyl-3,3-diphenyl-1H,3H-pyrrolo[1,2-c][1,3,2]oxazaborole | 277.2 g/mol | Theory 277 g | Theory 1.00 mol | Theory 1.00 equiv |

Procedure:

A 12-L flask fitted with a mechanical stirrer is charged with THF (1.0 L), water (600 mL), and (S)-diphenylprolinol sulfate (303 g, 1.00 mol). To the resultant slurry is added 5.0M aqueous NaOH (400 mL, 2.0 mol). The mixture is stirred at 20°–25° C. until all of the solid dissolves (ca. 0.5 h). Toluene (3.0 L) is added and the mixture stirred an additional 0.5 h. The entire mixture is filtered through a pad of celite (20 g).

The total amount of water used is important. Smaller quantities result in incomplete reaction and precipitation of sodium sulfate.

The filtration is necessary to remove a small amount of insoluble particles (molecular sieve fines) which interfere with the phase separation.

The filtrate is transferred into a 6-L extractor, and the aqueous layer (lower layer) removed. The organic layer is washed with water (500 mL).

The water wash results in a slight emulsion. The phase separation is improved if performed at 35°–40° C.

The organic layer is transferred to a 5-L flask equipped with an overhead stirrer, a nitrogen inlet tube, a teflon-coated thermocouple probe, and a distillation head connected to a wide-bore condenser. The organic layer is concentrated to a volume of 1.0 L (1 atmosphere).

The flask is graduated in 500 mL increments.

The concentration serves to both remove the THF and azeotropically dry the solution. The distillation begins with a pot temperature of 85° C. which slowly increases to 110° C. After the concentration is complete, the KF of the solution should be <50 μg/mL. If necessary, an additional toluene flush can be employed to further dry the solution.

The batch is cooled and stored under a nitrogen atmosphere, with rigorous exclusion of moisture. The solution of (S)-diphenylprolinol (free base) at 20° C. is diluted with dry toluene (1.0L, KF<20 μg/mL) followed by the slow addition of trimethylboroxine 4 (96 g, 0.765 mol) over a 0.5 h period.

The toluene is azeotropically dried (KF<20 μg/mL) just prior to use.

WARNING: The reaction is exothermic (>80 kcal/mol). Do not reduce the amount of toluene or add all of the trimethylboroxine at once.

During the addition the temperature of the mixture rises ca. 15° C. and an easily stirred white precipitate of intermediate 5 is formed. Identical results are obtained if the initial temperature of the batch is 35° C.

We have also used trimethylboroxine as a 15% (w/w) solution in THF (633 g, 95 g, 0.756 mol of trimethylboroxine) (Complex Chemical Corp., Seattle Wash.)

After the addition is complete, the mixture is aged 0.5 h. The mixture is diluted with toluene (1.0L, KF<20 μg/mL), and the batch then concentrated to a volume of 500 mL (1 atmosphere). The toluene is azeotropically dried (KF<20 μg/mL) just prior to use.

A nitrogen sweep is used to provide a flow of volatiles through the condenser and prevent the introduction of moisture. During the initial stages of the concentration the cooling water in the condenser must be turned off occasionally to prevent clogging with methylboronic acid.

The toluene addition (2.0 L, KF<20 μg/mL) followed by concentration is repeated to ensure complete removal of water and methylboronic acid.

The quality of the catalyst is determined by concentration of a sample (0.1 mL) in vacuo and examination of the $^1$H NMR (300 MHz, CDCl$_3$) spectrum. The spectrum should be free of resonances for diphenylprolinol ($\delta$ 4.3 (t)), trimethylboroxine ($\delta$ 0.45 (s)), intermediate 5 ($\delta$ 0.35 to $-0.50$ (multiple B-CH$_3$ singlets)), and water adduct 6 ($\delta$ $-0.25$ (broad B-CH$_3$ singlet)). The CDCl$_3$ must be molecular sieve dried and the sample must be handled under strictly anhydrous conditions. Examination of a sample after the first flush showed ca. 10% of intermediate 5 which was reduced to <3% after the second toluene flush.

The presence of diphenylprolinol in the toluene solution of oxazaborolidine 2 can also be determined by capillary GC: (DB-1,200° C.)<1% diphenylprolinol (rt 5.5 min); >99% oxazaborolidine 2 (rt 4.9 min).

A batch containing residual diphenylprolinol, intermediate 5, or water adduct 6 can be reconstituted by adding trimethylboroxine (5–10 mol %) and flushing with toluene.

The toluene solution of oxazaborolidine 2 is stored under nitrogen and rigidly protected from moisture.

It is imperative that the free oxazaborolidine catalyst be protected from moisture. Addition of water to oxazaborolidine 2 results in the formation of water adduct 6 which quickly disproportionates to intermediate 5 and diphenylprolinol, all of which significantly lower the enantioselection of ketone reductions.

For analysis, a portion of the toluene solution (10.0 mL) was concentrated in vacuo (50° C., 0.01 mBar) to afford 5.54 g of oxazaborolidine 2 as a white crystalline solid: mp 79°–81° C. [Lit. mp 74°–87° C.]; IR (CCl$_4$) 2960, 2880, 1440, 1330, 1310, 1235, 1000 cm$^{-1}$; $^1$H NMR (0.02M in CDCl$_3$) $\delta$ 7.65–7.15 (m, 10H, Ar-H), 4.4 (dd, J=5.8, 10.0 Hz, 1H, C3a-H), 3.45–3.30 (m, 1H, C6-H), 3.15–3.00 (m, 1H, C6-H), 1.90–1.55 (m, 3H, C4-H, C5-H$_2$), 0.95–0.75 (m, 1H, C4-H), 0.40 (s, 3H, B-CH$_3$); $^{13}$C NMR (0.02M in CDCl$_3$) $\delta$ 147.6, 144.0 (C1', C1''), 128.2, 127.7 (C3', C3'', C5', C5''), 127.1, 126.6 (C4', C4''), 126.3, 126.2 (C2', C2'', C6', C6''), 87.8 (C3), 72.7 (C3a), 42.9 (C6), 30.2 (C4), 26.4 (C5), $-5.6$ (br, B-CH$_3$); $^{11}$B NMR (0.02M in CDCl$_3$) $\delta$ 34.3. Anal. Calcd for C$_{18}$H$_{20}$BNO: C, 78.00; H, 7.27; N, 5.05. Found: C, 77.81; H, 7.37; N, 4.91.

EXAMPLE 2

Preparation of (S)-Tetrahydro-1-methyl-3,3-diphenyl-1H,3H-pyrrolo-[1,2-c]-[1,3,2]-oxazaborole Borane Adduct Reaction Scheme:

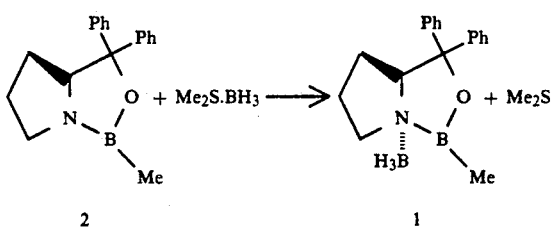

Materials:

| | | | | |
|---|---|---|---|---|
| (S)-Tetrahydro-1-methyl-3,3-diphenyl-1H,3H-pyrrolo[1,2-c][1,3,2]oxazaborole 2.0 M in toluene | 277.2 g/mol  2.00 M | (277 g)  500 mL | (1.00 mol)  1.00 mol | (1.00 equiv)  100 equiv |
| Borane dimethyl sulfide complex (BMS, Callery Chemical Company) | 10.0 M | 120 mL | 1.20 mol | 1.20 equiv |

| | -continued | | | |
|---|---|---|---|---|
| Hexane | | 3.00 L | | |
| (S)-Tetrahydro-1-methyl-3,3-diphenyl-1H,3H-pyrrolo[1,2-c][1,3,2]oxazaborole borane adduct | 291.0 g/mol | 260 g | 0.893 mol | 89.3% yield |

Procedure:

To a stirred solution of oxazaborolidine 2 in toluene (2.0M, 500 mL, 1.00 mol) is added BMS (10M, 120 mL, 1.20 mol) over a 15 min period.

The initial concentration of the solution is established by removing a known volume (typically 1.00 mL) and concentrating to a constant weight in vacuo (20° C., 0.01 mBar).

The reaction exotherms ca. 3°-5° C.

The mixture is aged for 0.5 h at 20°-25° C., then hexane (2.0 L) is added slowly over a 1 h period The hexane should be dry (KF<25 μg/mL). The product should form a dense crystalline solid which easily settles once stirring is discontinued.

The mixture is aged for 1 h at 20°-25° C., then cooled and aged for 3.5 h at −10° C. The mixture is filtered cold in a 3 L medium frit sintered glass Schlenk filter. The flask and cake are washed with dry hexane (2×500 mL), then dried in vacuo with a nitrogen purge (20°-25° C., ca. 100 mBar). Yield: 260 g (89.3%) of the title compound as a white, free-flowing crystalline solid.

The product is protected from moisture during the filtration by a nitrogen flow through the reaction vessel. A positive nitrogen pressure is used to push the mother liquors and wash solvent from the solid in the Schlenk filter.

The suitability of the catalyst is determined by $^1$H NMR. In CDCl$_3$ the borane adduct exists as a 90:10 mixture in equilibrium with the free oxazaborolidine. The CDCl$_3$ used for the spectrum must be dry.

Although not as sensitive to moisture as the free oxazaborolidine, the catalyst should be stored in a sealed container protected from moisture. In this manner, samples of the borane adduct have been stored for 1 yr at room temperature without noticeable degradation.

mp 124°-126° C. (dec)

$^1$H NMR (CDCl$_3$) δ 7.6 (m, 2H, Ar-H), 7.15-7.40 (m, 8H, Ar-H), 4.65 (t, J=7.9 Hz, 1H, C3a-H), 3.4 (m, 1H, C6-H), 3.2 (m, 1H, C6-H), 1.9 (m, 2H, C5-H$_2$), 1.7 (m, 1H, C4-H), 1.3 (m, 1H, C4-H), 2.1-0.8 (very br, 3H, BH$_3$), 0.78 (s, 3H, B-CH$_3$); $^{11}$B NMR (CDCl$_3$) δ 34.5 (OAB-BH$_3$), −14.5 (OAB-BH$_3$); $^{13}$C NMR (CDCl$_3$) δ 144.6 (C1'), 143.5 (C1''), 128.3 (C3', C5'), 128.2 (C3'', C5''), 127.4 (C4'), 127.1 (C4''), 125.4 (C2', C6'), 125.0 (C2'', C6''), 90.6 (C3), 76.2 (C3a), 57.7 (C6), 31.4 (C4), 25.0 (C5), −3.9 (br, B-CH$_3$).

Anal. Calcd for C$_{18}$H$_{23}$NOB$_2$: C, 74.29; H, 7.97; N, 4.81. Found: C, 74.34; H, 8.00; N, 4.69.

EXAMPLES 3-18

Following the procedures of the foregoing examples but substituting for the diarylprolinol of formula I the analogous compound wherein Ar is the substituent shown below, and substituting for trimethylboroxine of formula III the analogous boroxine wherein R is the substituent below, there are obtained in equivalent yields the correspondingly substituted compounds of formula V.

| | Ar | R |
|---|---|---|
| 3. | C$_6$H$_5$— | CH$_2$CH$_3$— |
| 4. | 4-F—C$_6$H$_4$— | CH$_3$— |
| 5. | 4-Cl—C$_6$H$_4$— | CH$_3$— |
| 6. | 4-CH$_3$—C$_6$H$_4$— | CH$_3$— |
| 7. | 4-CF$_3$—C$_6$H$_4$— | CH$_3$— |
| 8. | 4-t-Bu—C$_6$H$_4$— | CH$_3$— |
| 9. | 4-CH$_3$O—C$_6$H$_4$— | CH$_3$— |
| 10. | 3-Cl—C$_6$H$_4$— | CH$_3$— |
| 11. | 3,5-Cl$_2$—C$_6$H$_3$— | CH$_3$— |
| 12. | 3,5-(CH$_3$)$_2$—C$_6$H$_3$— | CH$_3$— |
| 13. | C$_6$H$_5$— | n-C$_4$H$_9$— |
| 14. | C$_6$H$_5$— | C$_6$H$_5$— |
| 15. | C$_6$H$_5$— | 4-F—C$_6$H$_4$— |
| 16. | C$_6$H$_5$— | 4-Cl—C$_6$H$_4$— |
| 17. | C$_6$H$_5$— | 4-CH$_3$—C$_6$H$_4$— |
| 18. | C$_6$H$_5$— | 4-CH$_3$O—C$_6$H$_4$— |

What is claimed is:

1. A method of preparing an oxazaborolidine-borane complex of formula V:

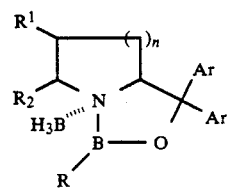

wherein:
Ar is
1) phenyl,
2) phenyl substituted in the meta- or para position with from 1 to 3 substituents selected from
    i) F, Cl or Br,
    ii) CF$_3$,
    iii) C$_{1-4}$ alkyl, and
    iv) C$_{1-4}$ alkoxy;
R$^1$ and R$^2$ are independently
1) H, or
2) C$_{1-3}$ alkyl; or
R$^1$ and R$^2$ together with carbon atoms to which they are bonded form a benzo group or a double bond;
R is C$_{1-4}$ alkyl or Ar; and
n is 1 or 2;
comprising adding a source of borane selected from borane dimethyl sulfide and gaseous diborane to a solution of oxazaborole of formula IV:

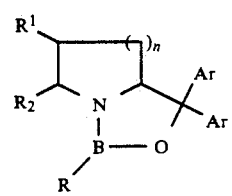

aging the resulting mixture, and adding a $C_{5-8}$ alkane to crystallize the oxazaborolidine-borane complex.

2. A method according to claim 1 wherein the source of borane is BMS.

3. A method according to claim 1 wherein the aging is continued until formation of the oxazaborolidine-borane complex is essentially complete.

4. A method according to claim 1 wherein the aging is continued for from about 10 minutes to about 2 hours.

5. A method according to claim 4 wherein the aging is continued for about 30 minutes.

6. A method according to claim 1 wherein the aging is continued at a temperature of from about 10° C. to about 35° C.

7. A method according to claim 1 wherein the oxazaborolidine-borane complex is aged following the addition of the $C_{5-8}$ alkane.

8. A method according to claim 7 wherein the aging is continued for from about 10 minutes to about 2 hours.

9. A method according to claim 7 wherein the aging is carried out at a temperature of from about 10° C. to about 35° C.

10. A method according to claim 7 wherein the aging is continued for about 1 hour at from about 20° C. to about 25° C.

11. A method according to claim 7 wherein the oxazaborolidine complex is cooled after completion of the aging.

12. A method according to claim 11 wherein the cooling is continued for from about 1 hour to about 10 hours.

13. A method according to claim 11 wherein the complex is cooled to below room temperature.

14. A method according to claim 13 wherein the complex is cooled to from about 0° C. to about −20° C.

* * * * *